(12) United States Patent
Fukushima et al.

(10) Patent No.: US 11,903,643 B2
(45) Date of Patent: Feb. 20, 2024

(54) LITHOTRIPSY APPARATUS AND LITHOTRIPSY SYSTEM

(71) Applicant: OLYMPUS CORPORATION, Tokyo (JP)

(72) Inventors: Ikutoshi Fukushima, Tokyo (JP); Atsuyoshi Shimamoto, Tokyo (JP); Mitsuru Namiki, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 247 days.

(21) Appl. No.: 17/406,412

(22) Filed: Aug. 19, 2021

(65) Prior Publication Data

US 2021/0378745 A1 Dec. 9, 2021

Related U.S. Application Data

(63) Continuation of application No. PCT/JP2019/007928, filed on Feb. 28, 2019.

(51) Int. Cl.
*A61B 18/26* (2006.01)
*A61B 90/00* (2016.01)
*A61B 18/00* (2006.01)

(52) U.S. Cl.
CPC .............. *A61B 18/26* (2013.01); *A61B 90/06* (2016.02); *A61B 2018/00505* (2013.01); *A61B 2018/00982* (2013.01); *A61B 2090/061* (2016.02)

(58) Field of Classification Search
CPC ..................... A61B 18/26; A61B 90/06; A61B 2018/00505; A61B 2018/00982;
(Continued)

(56) References Cited

U.S. PATENT DOCUMENTS 6,538,739 B1 3/2003 Visuri et al.
2014/0276101 A1* 9/2014 Asselin ............... A61B 5/4887
600/407

(Continued)

FOREIGN PATENT DOCUMENTS

JP 2001-517805 A 10/2001
JP 2017-500172 A 1/2017
(Continued)

OTHER PUBLICATIONS

International Search Report dated May 28, 2019 received in PCT/JP2019/007928.

*Primary Examiner* — Brian T Gedeon
*Assistant Examiner* — Joshua Andrew Schum-Houck
(74) *Attorney, Agent, or Firm* — Scully, Scott, Murphy & Presser, P.C.

(57) ABSTRACT

A lithotripsy apparatus includes: a treatment laser beam source that emits a treatment laser beam that crushes a stone; a guide light source that emits guide light; a photodetector that detects return light that returns as a result of the emitted guide light being reflected at the stone; and a processor including hardware, the processor being configured to: measure a distance from the treatment laser beam source to the stone on the basis of the return light; determine a condition of a bubble occurring between the treatment laser beam source and the stone on the basis of the measured distance; and adjust a light quantity of the treatment laser beam on the basis of the determined condition of the bubble.

19 Claims, 6 Drawing Sheets

(58) Field of Classification Search
CPC .... A61B 2090/061; A61B 2018/00535; A61B 2018/00625; A61B 2018/00642; A61B 2018/00672; A61B 2018/00678; A61B 2018/00702; A61B 2018/00785
See application file for complete search history.

(56) References Cited

U.S. PATENT DOCUMENTS

| | | |
|---|---|---|
| 2015/0133728 A1 | 5/2015 | Finkman et al. |
| 2015/0313444 A1 | 11/2015 | Wolf |
| 2015/0320433 A1* | 11/2015 | Navve .................. A61B 18/26 606/2.5 |
| 2016/0051125 A1 | 2/2016 | Wolf |
| 2016/0135894 A1 | 5/2016 | Finkman et al. |
| 2016/0361120 A1* | 12/2016 | Brinkmann .......... A61B 18/245 |
| 2017/0354464 A1 | 12/2017 | Waisman et al. |
| 2018/0092693 A1* | 4/2018 | Falkenstein ............ A61B 18/26 |

FOREIGN PATENT DOCUMENTS

| | | |
|---|---|---|
| JP | 2017-515561 A | 6/2017 |
| WO | 99/16366 A1 | 4/1999 |
| WO | 2015/069387 A1 | 5/2015 |
| WO | 2015/171289 A1 | 11/2015 |
| WO | 2017/212404 A1 | 12/2017 |

\* cited by examiner

LITHOTRIPSY APPARATUS AND LITHOTRIPSY SYSTEM

CROSS-REFERENCE TO RELATED APPLICATIONS

This is a continuation of International Application PCT/JP2019/007928 which is hereby incorporated by reference herein in its entirety.

TECHNICAL FIELD

The present invention relates to a lithotripsy apparatus and a lithotripsy system.

BACKGROUND ART

There are well-known apparatuses for crushing a stone by using a continuous pulsed laser beam (for example, refer to PTL 1).

In the apparatus disclosed in PTL 1, the quantity of return light resulting from a stone-crushing laser beam being reflected at the stone is used to measure the distance to the stone, so that the laser beam parameters are determined on the basis of the measured distance.

CITATION LIST

Patent Literature

{PTL 1}
USP Application Publication No. 2017/354464

SUMMARY OF INVENTION

One aspect of the present invention is a lithotripsy apparatus including: a treatment laser beam source that emits a treatment laser beam that crushes a stone; a guide light source that emits guide light; a photodetector that detects return light that returns as a result of the emitted guide light being reflected at the stone; and a processor including hardware, the processor being configured to: measure a distance from the treatment laser beam source to the stone on the basis of the return light; determine a condition of a bubble occurring between the treatment laser beam source and the stone on the basis of the measured distance; and adjust a light quantity of the treatment laser beam on the basis of the determined condition of the bubble.

In addition, another aspect of the present invention is a lithotripsy apparatus including: a treatment laser beam source that emits a treatment laser beam that crushes a stone; a guide light source that emits guide light; a photodetector that detects return light that returns as a result of the emitted guide light being reflected at the stone; a processor including hardware, the processor being configured to: measure a distance from the treatment laser beam source to the stone on the basis of the return light; and determined a condition of a bubble occurring between the treatment laser beam source and the stone on the basis of the measured distance; and a monitor that displays the determined condition of the bubble.

Furthermore, another aspect of the present invention is a lithotripsy method including: emitting a treatment laser beam that crushes a stone from a treatment laser beam source; emitting guide light from a guide light source; detecting return light that returns as a result of the emitted guide light being reflected at the stone; measuring a distance from the treatment laser beam source to the stone on the basis of the return light; determining a condition of a bubble occurring between the treatment laser beam source and the stone on the basis of the measured distance; and adjusting a light quantity of the treatment laser beam on the basis of the determined condition of the bubble.

DESCRIPTION OF EMBODIMENTS

A lithotripsy apparatus 3 and a lithotripsy system 1 according to one embodiment of the present invention will now be described with reference to the drawings.

Figure 1:
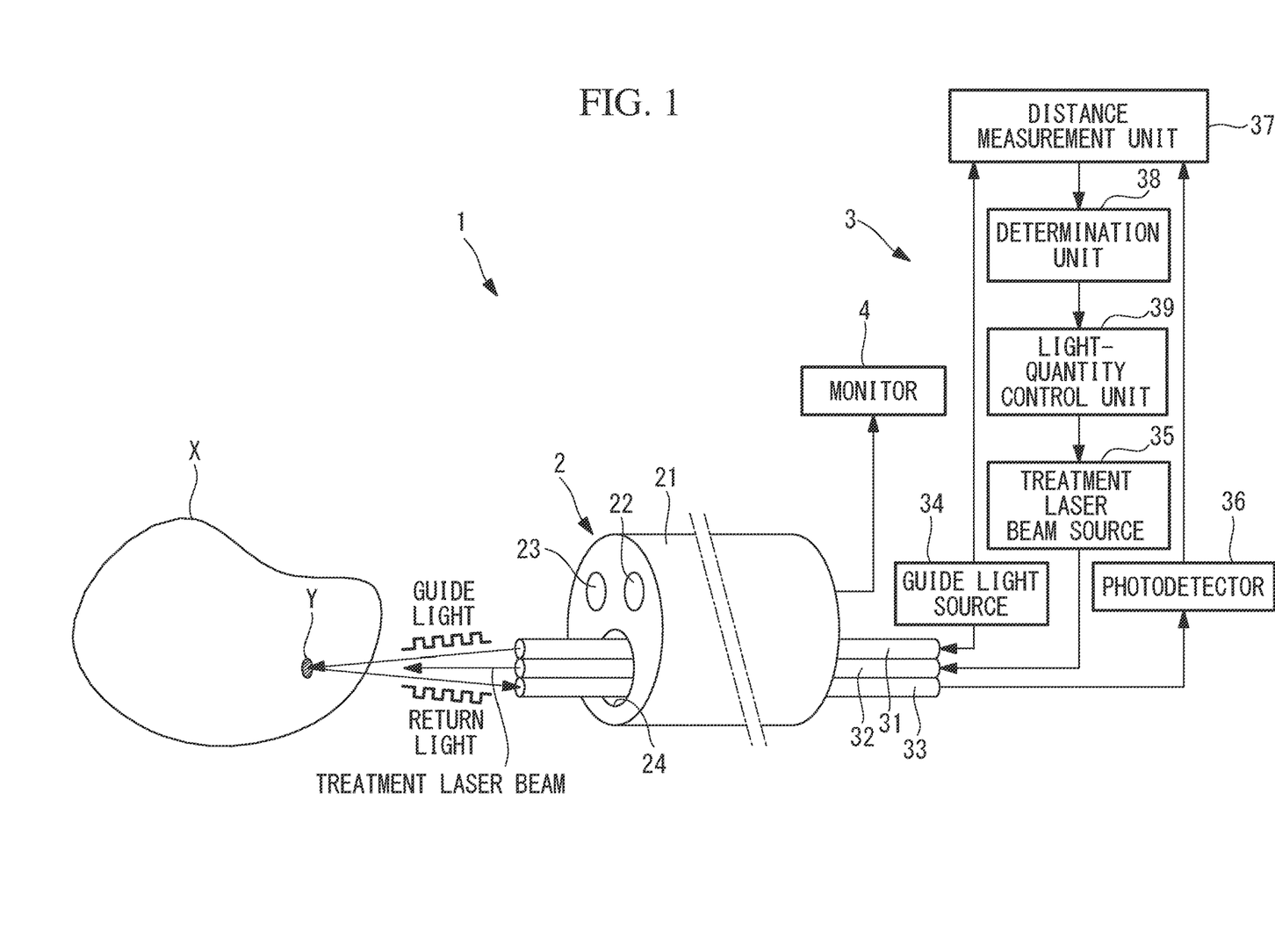
FIG. 1 is an overall configuration diagram showing a lithotripsy apparatus and a lithotripsy system according to one embodiment of the present invention.

As shown in FIG. 1, the lithotripsy system 1 according to this embodiment includes: an endoscope (image acquisition unit) 2; the lithotripsy apparatus 3 according to this embodiment; and a monitor (display unit) 4 for displaying an image G1 acquired by the endoscope 2.

The endoscope 2 includes: an illumination optical system 22 for irradiating a stone X in a body cavity with illumination light via a distal end of an insertion section 21 inserted into the body cavity; and an image-capturing optical system 23 for capturing an image of reflection light resulting from the illumination light being reflected at the stone X. The endoscope 2 further includes a channel 24 passing through the insertion section 21 along the longitudinal direction. Also, the endoscope 2 has a function for supplying normal saline from the basal end side thereof via the space in the channel 24, into which optical fibers 31, 32, and 33 (described later) are inserted, thereby perfusing the liquid in the body cavity.

The lithotripsy apparatus 3 includes the three single-mode optical fibers 31, 32, and 33, which are inserted into the channel 24 of the endoscope 2.

A guide light source (guide-light emission unit) 34 for emitting guide light is connected to the basal end side of the first optical fiber 31. A treatment laser beam source (laser-beam emission unit) 35 for emitting a treatment laser beam for crushing the stone X is connected to the basal end side of the second optical fiber 32. In addition, a photodetector (return-light detection unit) 36 that, of the return light returning as a result of the emitted guide light being reflected at the stone X, detects the return light coming via the distal end of the third optical fiber 33 is connected to the basal end side of the third optical fiber 33. The distal ends of the three optical fibers 31, 32, and 33 are aligned at the same position.

The guide light is pulsed light (e.g., green) in the visible light region, and the treatment laser beam is, for example, near infrared light. A position close or identical to the position, in the stone X, irradiated with the treatment laser beam is irradiated with the guide light, whereby a green spot Y having a different wavelength than the treatment laser beam is formed to visualize the position irradiated with the treatment laser beam.

A distance measurement unit 37 that measures, on the basis of the guide light and the return light, the distance between the stone X and the distal ends of the three optical fibers 31, 32, and 33, which emit guide light, is connected to the guide light source 34 and the photodetector 36.

The distance measurement unit 37 detects, by means of the photodetector 36, return light as a result of the guide light, which is a pulsed laser beam with a predetermined frequency emitted from the guide light source 34, returning from the stone X, thereby calculates the time from when the guide light is emitted from the guide light source 34 to when the return light is detected by the photodetector 36, and then obtains the distance by multiplying the calculated time by the light velocity and then by dividing the calculated result by two. In addition, in the case where there is a medium, such as normal saline, between the stone X and the optical fiber 33, a distance is calculated by taking the medium into account.

In addition, a determination unit 38 is connected to the distance measurement unit 37, and a light-quantity control unit 39 is connected to the determination unit 38.

The determination unit 38 determines the condition of a bubble occurring between the distal end of the third optical fiber 33 and the stone X on the basis of the distance measured by the distance measurement unit 37 in a state in which the treatment laser beam is being emitted.

More specifically, the determination unit 38 determines whether or not a temporal fluctuation in the distance measured by the distance measurement unit 37 has a period from a lower-limit period inclusive to an upper-limit period exclusive, i.e., the lower-limit and upper-limit periods defining a predetermined period range.

In the case where a temporal fluctuation in the distance has a period below the lower-limit period, it can be determined that the distance is too short for the light quantity of the treatment laser beam being emitted. On the other hand, in the case where the temporal fluctuation in the distance has a period equal to or larger than the upper-limit period, it can be determined that the distance is too long for the light quantity of the treatment laser beam being emitted. These determination results are displayed on the monitor 4.

The light-quantity control unit 39 is connected to the treatment laser beam source 35 and controls the treatment laser beam source 35 on the basis of the determination result in the determination unit 38, thereby increasing or decreasing the light quantity of the treatment laser beam emitted from the treatment laser beam source 35. In other words, the light-quantity control unit 39 decreases the light quantity of the treatment laser beam if it is determined in the determination unit 38 that the distance is too short. On the other hand, the light-quantity control unit 39 increases the light quantity of the treatment laser beam if it is determined in the determination unit 38 that the distance is too long.

In addition, the light-quantity control unit 39 can set a correction value on the basis of components of the liquid filling in the body cavity into which the endoscope 2 is inserted. In the case where a distance is measured by emitting guide light in a state in which no treatment laser beam is emitted, the light-quantity control unit 39 adjusts the light quantity of a treatment laser beam on the basis of the measured distance and the correction value. Here, the correction value may be the difference between the quantity of reflection light as a result of a treatment laser beam and/or guide light being reflected at the stone X in a state in which the treatment laser beam is being emitted and there is no bubble and the quantity of reflection light as a result of only guide light being reflected at the stone X in a state in which no treatment laser beam is being emitted.

The distance measurement unit 37, the determination unit 38, and the light-quantity control unit 39 are configured from processors.

The operation of the lithotripsy apparatus 3 and the lithotripsy system 1 according to this embodiment with the above-described configuration will be described below.

In order to crush the stone X formed in a body cavity, such as an urinary duct, by using the lithotripsy system 1 according to this embodiment, the endoscope 2 is inserted into the body cavity, and then, the image G1 of the interior of the body cavity is acquired by means of the image-capturing optical system 23 while the interior of the body cavity is being irradiated with illumination light from the illumination optical system 22, and the acquired image G1 is then displayed on the monitor 4.

While observing the image G1 on the monitor 4, an operator moves the endoscope 2 forward in the body cavity until the stone X appears in the image G1 and stops moving the endoscope 2 forward when the stone X appears in the image G1 on the monitor 4. In this state, the operator causes the three optical fibers 31, 32, and 33 to protrude from the distal end of the endoscope 2 via the channel 24 of the endoscope 2. Then, the operator operates the guide light source 34 in a state in which normal saline is perfused around the stone X, emits guide light via the first optical fiber 31, and adjusts the position of the endoscope 2 while observing the image G1 on the monitor 4, thus placing the spot Y of the guide light at a position to be irradiated with a treatment laser beam.

In this state, return light resulting from the guide light being reflected at the stone X is received by the third optical fiber 33 and is detected by the photodetector 36, and a distance is measured by the distance measurement unit 37 on the basis of the guide light emitted from the guide light source 34 and the return light detected by the photodetector 36.

According to this embodiment, a distance is measured on the basis of the Time of Flight method by using guide light, unlike the conventional technique in which a distance is measured on the basis of the light quantity of a treatment laser beam. Therefore, this embodiment affords an advantage in that a distance can be measured with high accuracy even if a laser beam is absorbed in a liquid that is present between the endoscope 2 and the stone X.

This embodiment affords another advantage in that because a distance is measured by means of guide light for visualizing the position irradiated with a treatment laser beam, it is possible to continue to measure a distance with high accuracy, regardless of a fluctuation in the light quantity of the treatment laser beam while the treatment laser beam is being emitted.

The measured distance is sent to the light-quantity control unit 39 and is corrected by using the set correction value, and the light quantity of the treatment laser beam is determined on the basis of the corrected distance.

The light-quantity control unit 39 controls the treatment laser beam source 35 and emits a treatment laser beam with the determined light quantity from the treatment laser beam source 35. By doing so, the position specified by guide light is irradiated with the treatment laser beam emitted from the second optical fiber 32, whereby crushing the stone X starts.

When a treatment laser beam is emitted from the distal end of the second optical fiber 32, the liquid disposed between the second optical fiber 32 and the stone X is instantly vaporized by energy of the treatment laser beam, thereby generating a bubble. The generated bubble is cooled by peripheral liquid and vanishes. Because the optical path length of guide light in the liquid and the optical path length of guide light in a bubble differ from each other, the distance measured by the distance measurement unit 37 fluctuates between when the guide light passes through the liquid and when the guide light passes through the bubble.

Figure 2:
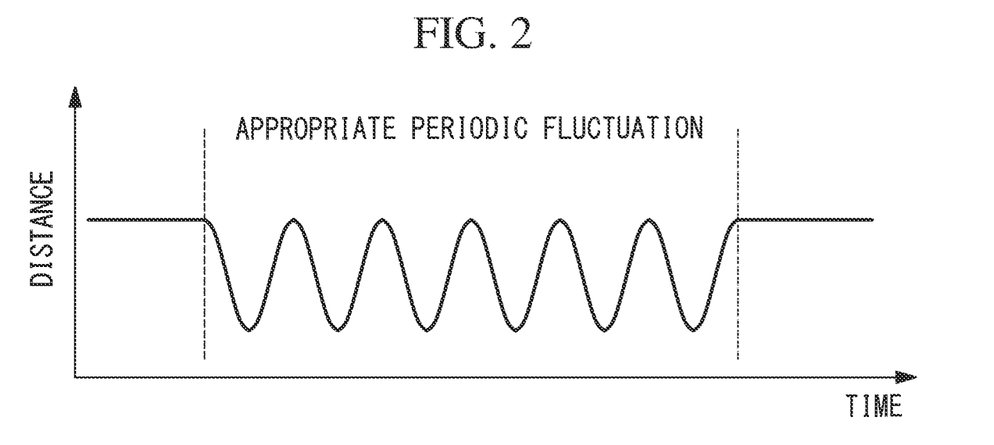
FIG. 2 is a diagram schematically showing one example of information on the distance that is measured by a distance measurement unit in a state in which a bubble with an appropriate size is formed while a treatment laser beam is being emitted from the lithotripsy apparatus in FIG. 1.
Figure 3:
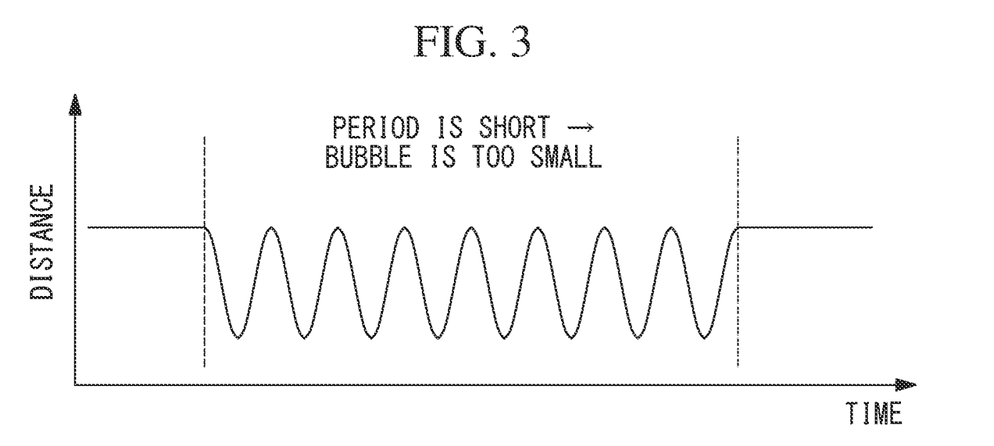
FIG. 3 is a diagram schematically showing one example of information on the distance that is measured by the distance measurement unit in a state in which a small bubble is formed while a treatment laser beam is being emitted from the lithotripsy apparatus in FIG. 1.
Figure 4:
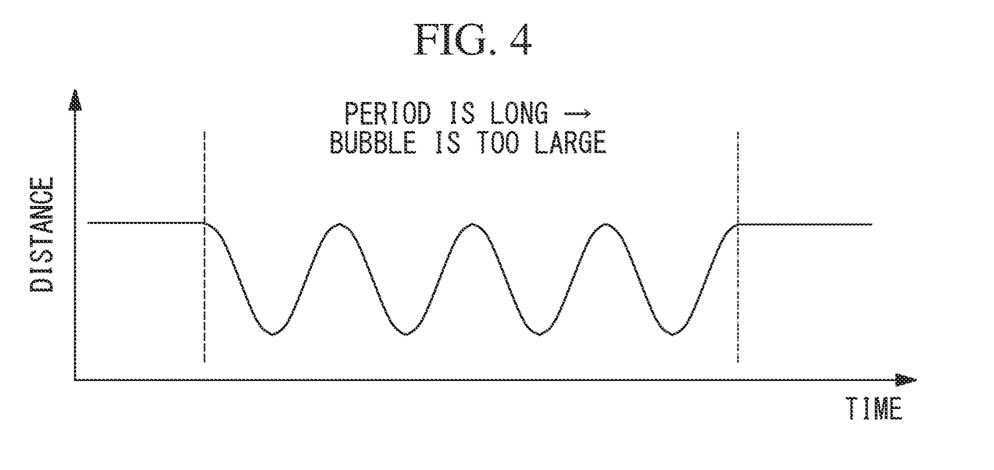
FIG. 4 is a diagram schematically showing one example of information on the distance that is measured by the distance measurement unit in a state in which a large bubble is formed while a treatment laser beam is being emitted from the lithotripsy apparatus in FIG. 1.

The pulse width of light used as guide light is on the order of tens of ns, whereas the period at which a bubble occurs is on the order of tens of μs. Because the time required to measure a distance by using guide light is sufficiently shorter than a period at which a bubble occurs and vanishes, the graph of the distance measured by the distance measurement unit 37 gives, as main data, frequency components that temporally fluctuate due to the occurrence and vanishment of a bubble, as shown in FIGS. 2 to 4. FIGS. 2 to 4 schematically show a temporal fluctuation in the distance. The graph of an actual distance contains high-frequency components that are higher than the main frequency components and does not exhibit a smooth fluctuation as shown in the figures. Nevertheless, main frequency components originating from a bubble is acquired by extracting periodically fluctuating components. The period at which a bubble occurs and vanishes is correlated with the size of the bubble. More specifically, the larger the size of a bubble, the longer the period at which the bubble occurs and vanishes. On the other hand, because a bubble occurs between the distal end of the optical fiber 32 and the stone X, the distance between the distal end of the optical fiber 32 and the stone X is correlated with the size of the bubble. In other words, the period of a temporal change in the measured distance is correlated with the distance between the distal end of the optical fiber 32 and the stone X.

In short, FIG. 2 shows a case where the distance fluctuates at an appropriate period within a prescribed range. In this case, a bubble with an appropriate size is formed between the second optical fiber 32 and the stone X.

FIG. 3 shows a case where the distance fluctuates at a period smaller than the lower-limit period of the prescribed range. This case shows that a bubble formed between the second optical fiber 32 and the stone X is small, indicating that the distance is too short.

FIG. 4 shows a case where the distance fluctuates at a period larger than the upper-limit period of the prescribed range. This case shows that a bubble formed between the second optical fiber 32 and the stone X is large, indicating that the distance is too long.

In the case of FIG. 3, the light-quantity control unit 39 controls the treatment laser beam source 35 so that the light quantity decreases. In the case of FIG. 4, on the other hand, the light-quantity control unit 39 controls the treatment laser beam source 35 so that the light quantity increases.

Thus, maintaining the state in which a bubble with an appropriate size is formed as shown in FIG. 2 provides an advantage in that when a treatment laser beam passes through the bubble, energy of the treatment laser beam is efficiently supplied to the stone X by suppressing absorption of the treatment laser beam into a liquid, making it possible to efficiently crush the stone.

Whether or not a bubble with an appropriate size is formed may be confirmed by allowing visible light having a plurality of different wavelengths to be selectively emitted from the guide light source 34, so that the color of the spot Y of the guide light may be set to "green" when a bubble with an appropriate size is formed or set to "red" when a bubble with an appropriate size is not formed, or alternatively by changing the color of the spot Y on the image G1 displayed on the monitor 4 without changing the color of the actual guide light. This can be achieved by configuring the guide light source 34 so as to emit visible light having a plurality of different wavelengths and so as to be connected to the determination unit 38 and then by changing the color of the emitted guide light on the basis of the determination result in the determination unit 38.

Although, in this embodiment, the first optical fiber 31 for guiding guide light, the second optical fiber 32 for guiding a treatment laser beam, and the third optical fiber 33 for guiding return light are configured from respective optical fibers, instead of this, a polarizing beam splitter and a dichroic mirror may be arranged on the basal end side of a single multicore optical fiber so that can the stone X be irradiated simultaneously with various types of light but also reflection light from the stone X can be made incident on the photodetector 36 by allowing all of the light to be guided via the single multicore optical fiber.

In addition, in the case where the amount of increase in the distance measured by the distance measurement unit 37 exceeds a predetermined threshold value, the light-quantity control unit 39 may decrease the light quantity of the treatment laser beam by controlling the treatment laser beam source 35.

If the distance increases significantly, it is assumed that energy of the treatment laser beam has moved the stone X towards the far side. Such unwanted movement of the stone X can be prevented by decreasing the light quantity of a treatment laser beam the next time the stone X is irradiated with a treatment laser beam under the same conditions.

Figure 5:
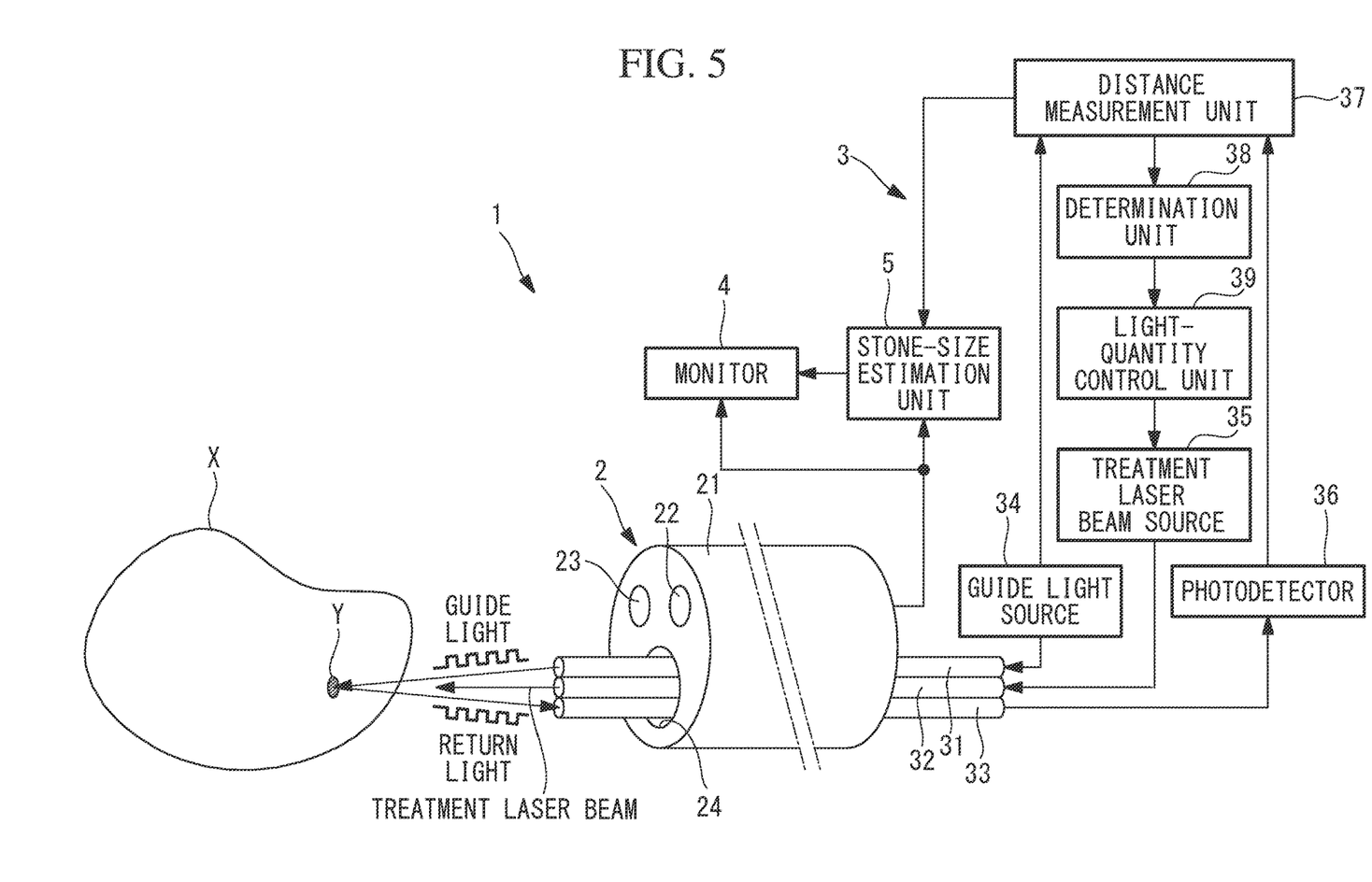
FIG. 5 is an overall configuration diagram showing a first modification of the lithotripsy apparatus and the lithotripsy system in FIG. 1.

In addition, as shown in FIG. 5, the lithotripsy system 1 according to this embodiment may include a stone-size estimation unit 5 for estimating the size of the stone X on the basis of the image G1 acquired by the image-capturing optical system 23 and the distance measured by the distance measurement unit 37 in a state in which no treatment laser beam is emitted and guide light is emitted. The stone-size estimation unit 5 may also be configured from a processor.

Then, the size of the stone X estimated by the stone-size estimation unit 5 is displayed on the monitor 4.

For the size of the stone X displayed on the monitor 4, any size, such as the maximum length dimension, perimeter, or area of the stone X appearing on the image G1, may be employed.

Figure 6:
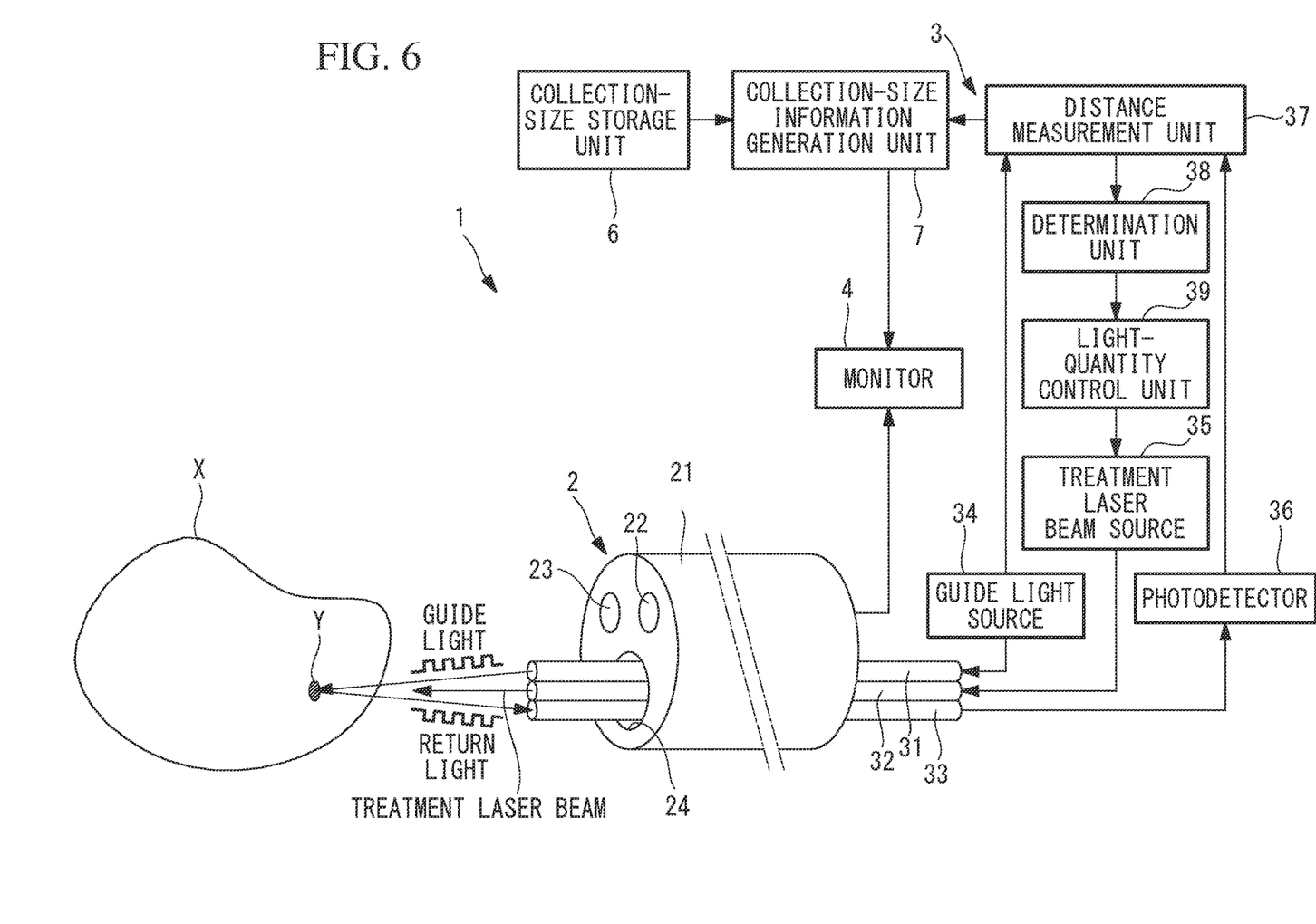
FIG. 6 is an overall configuration diagram showing a second modification of the lithotripsy apparatus and the lithotripsy system in FIG. 1.

In addition, when the stone is to be collected into the channel 24 by gripping the stone with collection means (not shown in the figure), such as basket forceps, that is made to protrude from or retract into the distal end of the channel (stone collection unit) 24, the lithotripsy system 1 may include the following configuration. More specifically, as shown in FIG. 6, the lithotripsy system 1 may include: a collection-size storage unit 6 for storing the size of the stone X that can be taken into the channel 24; and a collection-size information generation unit 7 for generating, on the basis of the distance measured by the distance measurement unit 37 and the collection size, information indicating a collection size that can be compared with the stone X.

Figure 7:
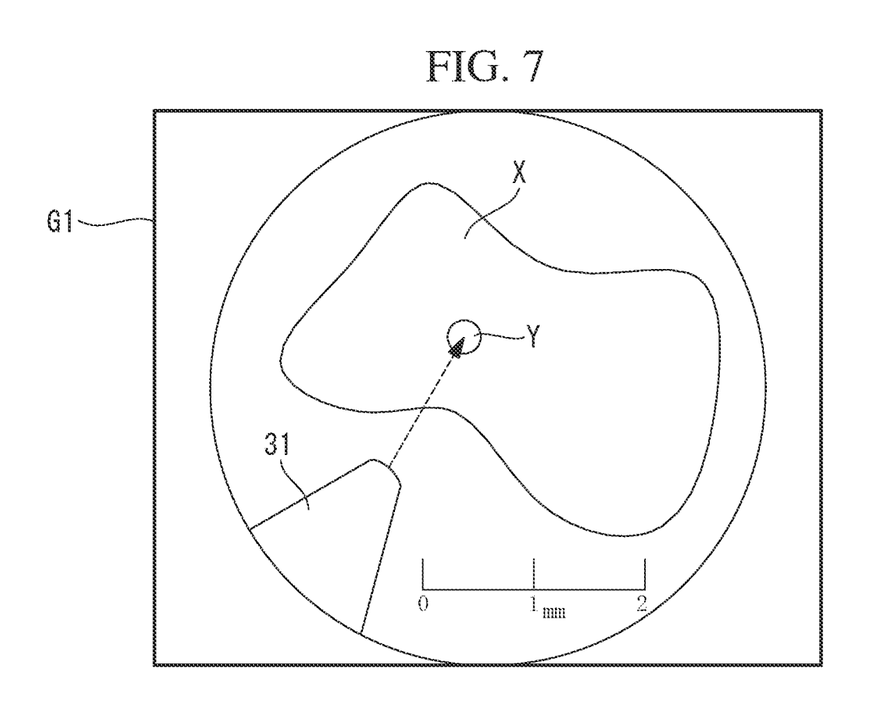
FIG. 7 is a diagram showing one example of information indicating a collection size comparable with a stone that is displayed together with an image on a monitor of the lithotripsy system in FIG. 6.
Figure 8:
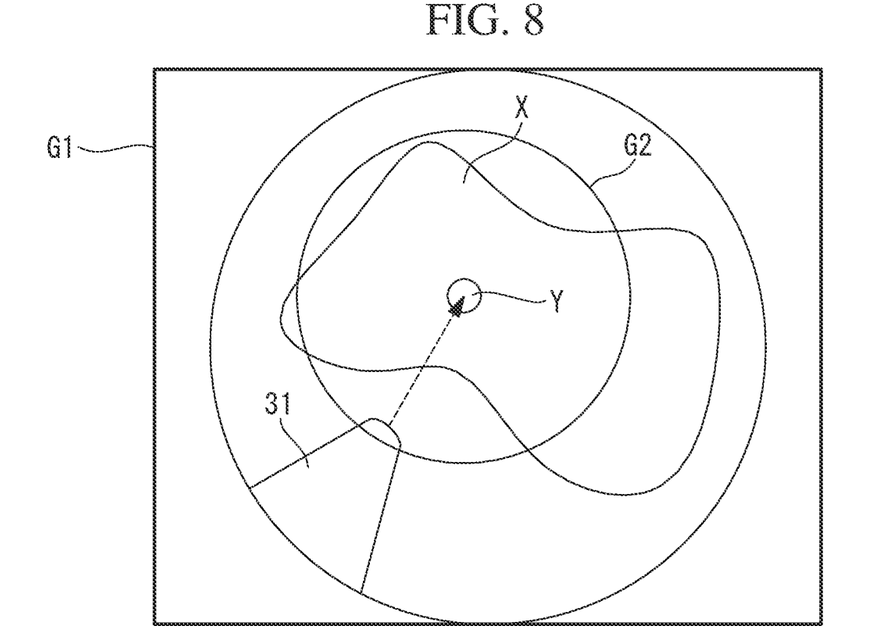
FIG. 8 is a diagram showing another example of information indicating a collection size comparable with a stone that is displayed together with an image on the monitor of the lithotripsy system in FIG. 6.

Information indicating a collection size that can be compared with the stone X may be realized by a scale, as shown in FIG. 7, or a virtual circular image G2, as shown in FIG. 8, having a size equal to the inner diameter of the channel 24. The operator can recognize the size of the stone X by superimposing the scale on the image G1 displayed on the monitor 4 and then comparing the stone X with the scale. In addition, by superimposing the virtual circular image G2 on the image G1 of the stone X displayed on the monitor 4, the operator can easily determine that the stone X can be collected if the stone X is so small as to fit into the virtual circular image G2 or the stone X cannot be collected if the stone X is too large to fit into the virtual circular image G2.

The collection-size storage unit 6 is configured from a memory, and the collection-size information generation unit 7 is configured from a processor.

According to this lithotripsy system 1, because it is not necessary to process the image G1 acquired by the endoscope 2, it is possible to easily provide information that allows the operator to determine whether or not the stone X has been crushed to a size small enough to be collected.

As the stone collection unit, a sheath that allows basket forceps to pass therethrough so that the basket forceps can protrude from and retract into the sheath may be employed, instead of the channel 24.

Figure 9:
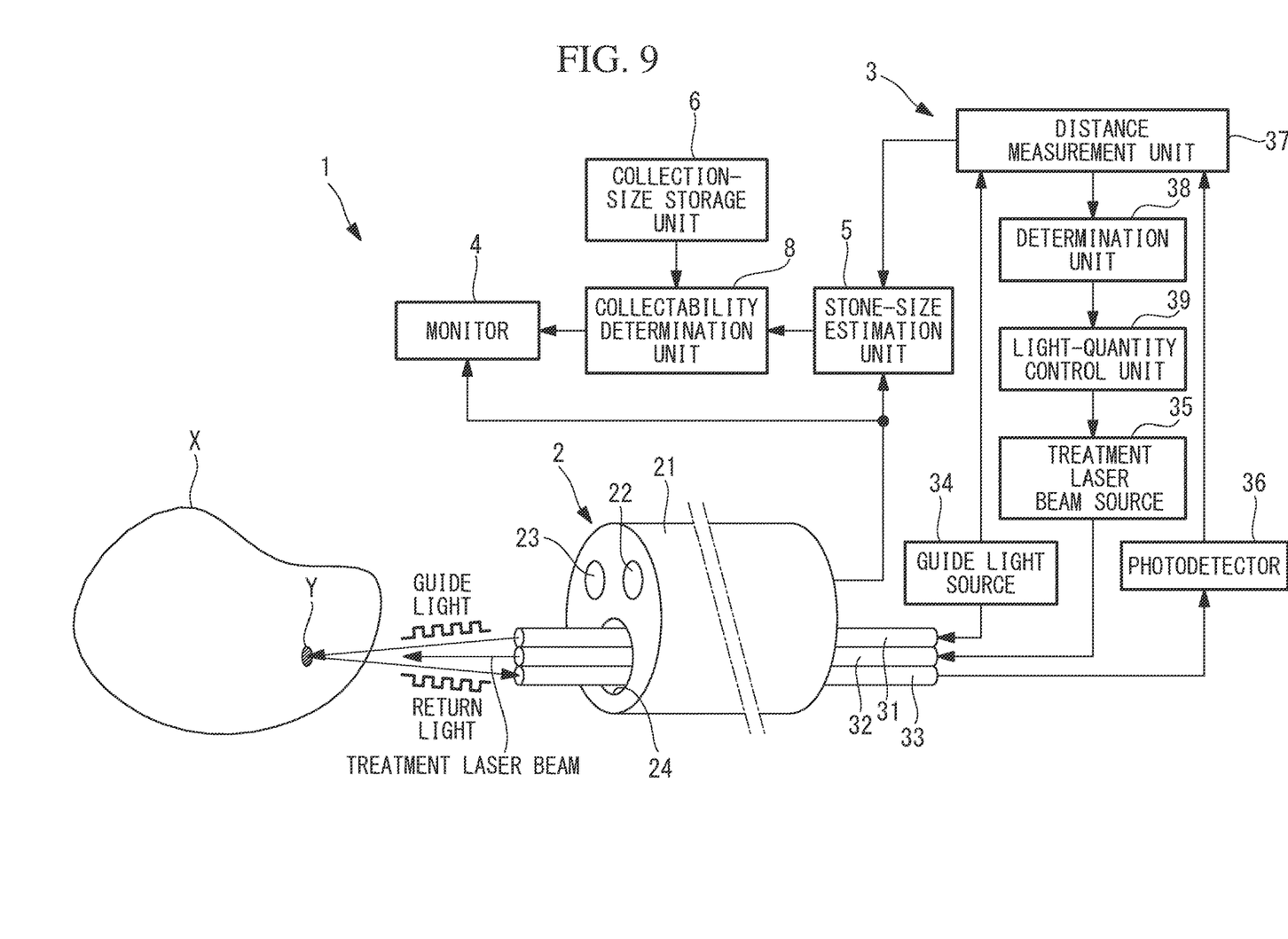
FIG. 9 is an overall configuration diagram showing a third modification of the lithotripsy apparatus and the lithotripsy system in FIG. 1.

In addition, instead of displaying information indicating a collection size on the monitor 4, the lithotripsy system 1 may include a collectability determination unit 8, as shown in FIG. 9, for determining whether or not the stone X can be collected into the channel 24 on the basis of the estimated size of the stone X and the collection size, thereby displaying, on the monitor 4, a determination result provided by the collectability determination unit 8. As the determination result, a character string, such as "Collectable" or "Not collectable", audio, a red or green illuminating indicator, or the like can be employed. On the basis of the determination result displayed on the monitor 4 or the like, the operator can quickly and correctly confirm whether or not the stone X can be collected.

Although this embodiment employs the urinary duct as the body cavity to which the lithotripsy apparatus 3 and the lithotripsy system 1 are applied, instead of this, the lithotripsy apparatus 3 and the lithotripsy system 1 can be applied to the bile duct or any other body cavity.

In addition, although this embodiment has been described so that the light quantity of a treatment laser beam is adjusted by the light-quantity control unit 39 in the case where a bubble with an appropriate size cannot be formed, instead of this, a determination result as to the condition of a bubble may be displayed on the monitor 4, thereby prompting the operator to manually adjust the light quantity. In this case, a determination result may be displayed by changing the color of the spot Y of guide light as described above.

In addition, although this embodiment has been described so that the light quantity of a treatment laser beam is increased or decreased in the case where a bubble with an appropriate size cannot be formed, instead of this, the distance between the lithotripsy apparatus 3 and the stone X may be adjusted on the basis of a determination result as to the condition of the bubble.

Distance adjustment may be performed via electrical driving by providing an adjustment mechanism, or alternatively, instruction information, such as "Move the optical fiber away from the stone" or "Move the optical fiber closer to the stone", based on the determination result may be displayed on the monitor 4, thereby prompting the operator to perform distance adjustment.

More specifically, when the distance measured by the distance measurement unit 37 indicates that a small bubble is formed as shown in FIG. 3, it is preferable that the distance be increased. On the other hand, when the distance measured by the distance measurement unit 37 indicates that a large bubble is formed as shown in FIG. 4, it is preferable that the distance be decreased.

Note that the following aspects can be derived from this embodiment.

One aspect of the present invention is a lithotripsy apparatus including: a laser-beam emission unit for emitting a treatment laser beam that crushes a stone; a guide-light emission unit for emitting guide light; a return-light detection unit for detecting return light that returns as a result of the emitted guide light being reflected at the stone; a distance measurement unit for measuring the distance from the laser-beam emission unit to the stone on the basis of the return light; a determination unit for determining a condition of a bubble occurring between the laser-beam emission unit and the stone on the basis of the distance measured by the distance measurement unit; and a light-quantity control unit for adjusting the light quantity of the treatment laser beam on the basis of the determined condition of the bubble.

According to this aspect, return light, which is light returning from the stone as a result of guide light emitted from the guide-light emission unit being reflected at the stone, is detected by the return-light detection unit, thereby visualizing the position, in the stone, irradiated with the laser beam. In addition, the distance from the laser-beam emission unit to the stone is measured by the distance measurement unit on the basis of the return light detected by the return-light detection unit.

When a treatment laser beam having a light quantity according to the measured distance is emitted from the laser-beam emission unit, the liquid present before the stone is vaporized, generating a bubble. Because the air-equivalent length in the case where guide light passes through the liquid differs from the distance in the case where guide light passes through the bubble, the distance measured by the distance measurement unit periodically fluctuates due to occurrence and vanishment of a bubble.

The period at which the distance measured by the distance measurement unit fluctuates has a relationship with the size of the bubble. More specifically, the larger the bubble, the longer the air-equivalent length, and hence, each time a bubble occurs, the measured distance is repeatedly increased and decreased at substantially constant pitches at a period according to the size of the bubble. By allowing the determination unit to determine the condition of the bubble on the basis of such a periodic fluctuation in the distance, the stone can be irradiated with a laser beam under conditions that allow a bubble with an appropriate size to be formed, whereby the stone can be efficiently crushed.

In the above-described aspect, the determination unit may determine the condition of the bubble on the basis of whether or not the amount of a temporal change in the distance measured by the distance measurement unit is within a predetermined range.

With the light quantity of a laser beam being constant, the period at which a bubble occurs and vanishes is long when the generated bubble is large, and the period at which a bubble occurs and vanishes is short when the generated bubble is small.

Therefore, according to the determination result as to the condition of the bubble based on a temporal fluctuation in the measured distance, the light quantity of the laser beam emitted from the laser-beam emission unit is increased when the temporal fluctuation in the distance is greater than a predetermined threshold value, and the light quantity of the laser beam emitted from the laser-beam emission unit is decreased when the temporal fluctuation in the distance is smaller than or equal to the predetermined threshold value. By doing so, the stone can be irradiated with a laser beam under conditions that allow a bubble with an appropriate size to be formed, whereby the stone can be efficiently crushed.

In addition, in the above-described aspect, the light-quantity control unit may decrease the light quantity of the treatment laser beam when the amount of change in the distance is aperiodic and exceeds a predetermined threshold value.

With this configuration, when the distance measured on the basis of return light of guide light changes by a large amount while a treatment laser beam is being emitted, it can be safely assumed that the stone has been moved towards the far side by the power of the treatment laser beam. Therefore, the next time the stone is irradiated with a treatment laser beam, it is possible to prevent the stone from moving similarly towards the far side by decreasing the light quantity of the treatment laser beam.

In addition, another aspect of the present invention is a lithotripsy apparatus including: a laser-beam emission unit for emitting a treatment laser beam that crushes a stone; a guide-light emission unit for emitting guide light; a return-light detection unit for detecting return light that returns as a result of the emitted guide light being reflected at the stone; a determination unit for determining a condition of a bubble occurring between the laser-beam emission unit and the stone on the basis of the distance measured by the distance measurement unit; and a display unit for displaying the determined condition of the bubble.

In the above-described aspect, the guide light may visualize the position, in the stone, irradiated with the treatment laser beam in a color according to the determination result from the determination unit.

With this configuration, the operator can determine whether the distance to the stone is larger or smaller than the predetermined range by observing the color of the guide light displayed on the display unit.

In addition, in any of the above-described aspects, the distance measurement unit may measure the distance by the Time of Flight method.

With this configuration, even when the guide light and return light suffer a decrease in the quantity as a result of being absorbed into the liquid present between the guide-light emission unit and the stone, a distance can be measured with high accuracy.

In addition, another aspect of the present invention is a lithotripsy system including: one of above-described lithotripsy apparatuses; an image acquisition unit for acquiring an image of the stone; and a display unit for displaying the acquired image.

According to this aspect, an image of the stone acquired by the image acquisition unit is displayed on the display unit. Because the position irradiated with the treatment laser beam is visualized on the image of the stone by means of guide light emitted from the guide-light emission unit, the operator can focus guide light on a desired position in the stone by operating the lithotripsy apparatus, thereby irradiating the desired position with a treatment laser beam.

The above-described aspect may further include: a stone-size estimation unit for estimating the size of the stone on the basis of the image acquired by the image acquisition unit and the distance measured by the distance measurement unit, wherein the display unit may display the size of the stone estimated by the stone-size estimation unit.

With this configuration, the stone-size estimation unit can detect the contour shape of the stone by processing the image acquired by the image acquisition unit and highly accurately estimate an actual size, such as the maximum dimension of the contour shape, of the stone by using the distance measured by the distance measurement unit. By displaying, on the display unit, the size of the stone estimated in this manner, the operator can easily determine whether or not the stone has been satisfactorily crushed.

In addition, the above-described aspect may further include: a stone collection unit for collecting the stone; a collection-size storage unit for storing a collection size, which indicates a size of the stone that can be collected by the stone collection unit; and a collection-size information generation unit for generating, on the basis of the distance measured by the distance measurement unit and the collection size, information indicating a collection size that can be compared with the stone, wherein the display unit may display the information indicating the collection size.

With this configuration, information indicating a collection size that can be compared with the stone is generated by the collection-size information generation unit on the basis of the collection size stored in the collection-size storage unit and the distance measured by the distance measurement unit in a state in which no treatment laser beam is being emitted and guide light is being emitted. By comparing the image of the stone displayed on the display unit with the information indicating a collection size, the operator can continue crushing the stone until the stone size is smaller than or equal to the collection size. By doing so, the stone can be collected by the stone collection unit after having been crushed through minimum required crushing.

In addition, in the above-described aspect, the collection-size information generation unit may generate a virtual image indicating the collection size, and the display unit may display the virtual image such that the virtual image is superimposed on the image of the stone.

With this configuration, because a virtual image indicating the collection size and an image of the stone are displayed in an overlaid manner on the display unit, the operator can easily confirm whether or not the stone has been crushed to a collectable size by comparing these images.

In addition, the above-described aspect may further include: a stone-size estimation unit for estimating the size of the stone on the basis of the image acquired by the image acquisition unit and the distance measured by the distance measurement unit in a state in which no treatment laser beam is being emitted and guide light is being emitted; and a collectability determination unit for determining whether or not the stone can be collected by the stone collection unit on the basis of the size of the stone estimated by the stone-size estimation unit and the collection size, wherein the display unit may display a determination result from the collectability determination unit.

With this configuration, the stone-size estimation unit estimates the size of the stone on the basis of the image of the stone and the measured distance, and the estimated size of the stone and the collection size are compared in the collectability determination unit, whereby it is determined whether or not the stone can be collected. Then, when the determination result is displayed on the display unit, the operator can easily confirm whether or not the stone has been crushed to a collectable size.

REFERENCE SIGNS LIST

1 Lithotripsy system
2 Endoscope (image acquisition unit)
3 Lithotripsy apparatus
4 Monitor (display unit)
5 Stone-size estimation unit
6 Collection-size storage unit
7 Collection-size information generation unit
8 Collectability determination unit
24 Channel (stone collection unit)
34 Guide light source (guide-light emission unit)
35 Treatment laser beam source (laser-beam emission unit)
36 Photodetector (return-light detection unit)
37 Distance measurement unit
38 Determination unit
39 Light-quantity control unit
G1 Image
G2 Virtual image
X Stone

The invention claimed is:

1. A lithotripsy apparatus comprising:
a treatment laser beam source configured to emit a treatment laser beam for crushing a stone;
a guide light source configured to emit a guide light;
a photodetector configured to detect a return light including the guide light reflected by the stone; and
a processor comprising hardware, the processor being configured to:
calculate a distance from the treatment laser beam source to the stone on the basis of the return light;
determine whether a temporal fluctuation in the distance calculated is equal to or less than a threshold value; and
in response to determining that the temporal fluctuation in the distance calculated is equal to or less than the threshold value, control the treatment laser beam source to decrease a light quantity of the treatment laser beam.

2. The lithotripsy apparatus according to claim 1,
wherein the processor is configured to control the treatment laser beam source to increase the light quantity of the treatment laser beam in response to determining that the temporal fluctuation in the distance calculated is not equal to or less than the threshold value.

3. A lithotripsy system comprising:
the lithotripsy apparatus according to claim 2; and
an endoscope configured to:
acquire an image of the stone; and
control a monitor to display the image.

4. The lithotripsy apparatus according to claim 1,
wherein the processor is configured to:
determine whether an amount of change in the distance calculated is aperiodic and exceeds a threshold value; and
in response to determining that the amount of change in the distance calculated is aperiodic and exceeds the threshold value, control the treatment laser beam source to decrease the light quantity of the treatment laser beam.

5. A lithotripsy system comprising:
the lithotripsy apparatus according to claim 1; and
an endoscope configured to:
acquire an image of the stone; and
control a monitor to display the acquired image.

6. The lithotripsy system according to claim 5,
wherein the processor is configured to:
estimate a size of the stone on the basis of the image acquired by the endoscope and the distance calculated; and
control the monitor to display the size of the stone estimated.

7. A lithotripsy system comprising:
the lithotripsy apparatus according to claim 1; and
an endoscope configured to:
acquire an image of the stone; and
control a monitor to display the image.

8. A lithotripsy apparatus comprising:
a treatment laser beam source configured to emit a treatment laser beam for crushing a stone;
a guide light source configured to emit a guide light;
a photodetector configured to detect a return light including the guide light reflected by the stone; and
a processor comprising hardware, the processor being configured to:
calculate a distance from the treatment laser beam source to the stone on the basis of the return light;
determine whether an amount of change in the distance calculated is aperiodic and exceeds a threshold value; and
in response to determining that the amount of change in the distance calculated is aperiodic and exceeds the threshold value, control the treatment laser beam source to decrease the light quantity of the treatment laser beam.

9. The lithotripsy apparatus according to claim 8,
wherein the processor is configured to:
determine whether a temporal fluctuation in the distance calculated is greater than the threshold value; and
in response to determining that the temporal fluctuation in the distance calculated is greater than the threshold value, control the treatment laser beam source to increase the light quantity of the treatment laser beam.

10. A lithotripsy system comprising:
the lithotripsy apparatus according to claim 9; and
an endoscope configured to:
acquire an image of the stone; and
control a monitor to display the image.

11. The lithotripsy apparatus according to claim 8, wherein the guide light visualizes the position, in the stone, irradiated with the treatment laser beam in a color according to a determination result by the processor.

12. A lithotripsy system comprising:
the lithotripsy apparatus according to claim 8; and
an endoscope configured to acquire an image of the stone.

13. The lithotripsy system according to claim 12, wherein the processor is configured to:
estimate a size of the stone on the basis of the image acquired by the endoscope and the measured distance; and
control a monitor to display the size of the stone estimated.

14. The lithotripsy apparatus according to claim 8, wherein the processor is configured to:
determine a condition of a bubble occurring between the treatment laser beam source and the stone on the basis of the measured distance; and
control a monitor to display the condition of the bubble determined.

15. A lithotripsy method comprising:
controlling a treatment laser beam source to emit a treatment laser beam for crushing a stone;
controlling a guide light source to emit a guide light;
control a photodetector to detect a return light including the guide light reflected by the stone;
calculating a distance from the treatment laser beam source to the stone on the basis of the return light;
determining a temporal fluctuation in the distance calculated is equal to or less than a threshold value; and
in response to determining that the temporal fluctuation in the distance calculated is equal to or less than the threshold value, controlling the treatment laser beam source to decrease a light quantity of the treatment laser beam.

16. The lithotripsy method according to claim 15, further comprising:
determining a condition of a bubble on the basis of the temporal fluctuation in the distance calculated; and
controlling a monitor to display the condition of the bubble determined.

17. The lithotripsy method according to claim 15, further comprising:
determining whether an amount of change in the distance calculated is aperiodic and exceeds a threshold value; and
in response to determining that the amount of change in the distance calculated is aperiodic and exceeds a threshold value, controlling the treatment laser beam source to decrease the light quantity of the treatment laser beam.

18. The lithotripsy method according to claim 15, further comprising:
acquiring an image of the stone; and
controlling a monitor to display the image acquired.

19. The lithotripsy method according to claim 18, further comprising:
estimating a size of the stone on the basis of the image acquired and the measured distance; and
controlling the monitor to display the size of the stone estimated.

* * * * *